United States Patent [19]
Fujieda et al.

[11] Patent Number: 5,528,323
[45] Date of Patent: Jun. 18, 1996

[54] OPHTHALMIC APPARATUS INCLUDING HAND-HELD MEASURING DEVICE AND WIRELESS DATA TRANSMISSION

[75] Inventors: Masanao Fujieda, Tohohashi; Naoki Isogai, Nishio; Yoshiaki Mimura; Masamichi Suzuki, both of Gamagori, all of Japan

[73] Assignee: Nidek Co., Ltd., Japan

[21] Appl. No.: 142,941

[22] Filed: Oct. 29, 1993

[30] Foreign Application Priority Data

Oct. 30, 1992 [JP] Japan ................................. 4-316407
May 31, 1993 [JP] Japan ................................. 5-154420

[51] Int. Cl.⁶ ........................................................ A61B 3/10
[52] U.S. Cl. ........................... 351/218; 351/211; 351/212
[58] Field of Search ................................. 351/20i0, 205, 351/211, 212, 218, 221

[56] References Cited

U.S. PATENT DOCUMENTS 4,580,559  4/1986  L'Esperance ..................... 351/217 X
4,861,156  8/1989  Terry ............................... 351/243
5,011,276  4/1991  Iwamoto ............................ 351/211
5,420,652  5/1995  Fujieda ............................. 351/239

FOREIGN PATENT DOCUMENTS 5-154103  6/1993  Japan.

Primary Examiner—William L. Sikes
Assistant Examiner—Hung Xuan Dang
Attorney, Agent, or Firm—Finnegan, Henderson, Farabow, Garrett & Dunner

[57] ABSTRACT

An ophthalmic apparatus is provided with a measurement unit that includes a measurement device that projects measurement light onto an examinee's eye and detects the measurement light reflected by the examinee's eye, a grip that supports the measurement device, so that the examiner can hold the device in his hand, a wireless transmitting device that transmits data about the examinee's eye to a receiving device separate from the measurement unit, the data being obtained based on light detected by the measurement device, and a signal generating device that generates a start signal to make the transmitting device start to transmit; the receiving device receives the transmitted data about the examinee's eye and has a holding device that detachably holds the measurement unit for transmission of measurement data.

14 Claims, 7 Drawing Sheets

OPHTHALMIC APPARATUS INCLUDING HAND-HELD MEASURING DEVICE AND WIRELESS DATA TRANSMISSION

BACKGROUND OF THE INVENTION

1. Field of the Invention

The present invention relates to a type of ophthalmic apparatus in which the components are separated, a representative thereof being a hand-held apparatus and a receiver, and more particularly, relates to ophthalmic apparatus capable of wireless communication between the components.

2. Description of Related Art

Ophthalmic examining apparatus, for instance, an objective type, refracting power measurement apparatus and a cornea shape measurement apparatus or the like, consists of various parts such as an observing part, measuring part, displaying part and recording part. Such ophthalmic apparatus comprising so many parts can be large and heavy, and not easily moved about.

The recent rapid progress of electronics, however, has enabled miniaturization of various devices and, even in the ophthalmic field, miniaturization of hand-held type apparatus for examining the eye.

As a hand-held type of ophthalmic apparatus, known are apparatus for mainly observing, such as a retinoscope and an ophthalmoscope or the like, and recently, a hand-held type of apparatus having a measuring system which can be miniaturized, an example of which is a contact type tonometer.

A hand-held type ophthalmic apparatus that includes a measurement system for measuring tension of an eye or other uses ought to be compact and light in order to be easily portable and not burdened with additional apparatus, e.g., a printer, and thus increased weight. Accordingly, conceivable is apparatus that is separated into a unit comprising internal measurement with a data displaying system and another unit such as a printing device and the like, which is kept separate because of weight and other factors. For communication of measurement data between units of such separate type apparatus, most easily, the units are connected with each other by cables; RS-232C for serial communication, Centronics for parallel communication for example).

Commonly, ophthalmic apparatus comprising a measurement system is also provided with other systems for displaying, recording measured data and transmitting such data to a host computer. However, conventional hand-held type apparatus, being not provided with recording and data transmitting systems, can not be used in the same manner as general apparatus.

If the measuring and other units are connected with each other by cables, there occurs the problem that these cables may be an obstacle to measurement operation, and the maintenance of a cable can be difficult because a cable is liable to break down.

SUMMARY OF THE INVENTION

The present invention has been made in view of the above circumstances and has an object to overcome the above problems by providing an ophthalmic apparatus which is in part portable yet provided with a system similar to conventional apparatus, for instance by having a recording system and other features.

Another object of the present invention is providing an ophthalmic apparatus comprising a measurement unit and another separate unit containing a printer and other apparatus, and capable of providing wireless communication between both units, i.e., without connecting by cable.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the objects and in accordance with the purpose of the invention, as embodied and broadly described herein, an ophthalmic apparatus of this invention comprises (A) a hand-held measurement unit comprising measurement means for projecting measurement light to an examinee's eye and detecting the measurement light reflected by the examinee's eye, and means for processing the detected measurement light to provide measurement data, a hand-grip designed to be held by an examiner for placement of the measurement means, wireless transmitting means for transmitting the measurement data to a receiving means separate from the measurement unit, signal generating means for generating a start signal to initiate transmission of measurement data from the transmitting means, display means for displaying the measurement data, a battery for supplying electric power to the measurement unit, a receiving device separate from the measurement unit and having the receiving means for receiving the measurement data, and a holding means for detachably holding the hand-held measurement unit during transmission of measurement data.

In another aspect of the present invention, an ophthalmic apparatus comprises, a hand-held measurement unit comprising, a measurement optical system for projecting luminous flux to an examinee's eye and receiving the luminous flux reflected by the examinee's eye at an optical detecting element, a hand-grip for supporting the measurement optical system, and designed to be held by an examiner in his hand, optical transmitting means for transmitting measurement data of the examinee's eye to an optical receiving means separate from the measurement unit, the measurement data being obtained based on reflected luminous flux received by the measurement optical system, and signal generating means for generating a start signal to initiate transmission of measurement data from the optical transmitting means, a light source for the measurement optical system, the light source used in common with the optical transmitting means, and a mode changing switch and control circuit changing means for controlling the turning on and off of the light source by the mode changing switch thereby to permit switching between the measurement mode and the optical transmission mode, a receiving unit having the optical receiving means for receiving the measuremet data about the examinee's eye, and holding means for detachably holding the measurement unit during transmission of measurement data.

And further, in the third aspect of an ophthalmic apparatus of the present invention comprises a measurement unit and a printer unit, the measurement unit being portable via one hand of an examiner and comprising, an index projecting optical system for projecting index light for measuring the corneal shape of an examinee's eye, and including an index projecting light source and a measurement control circuit, a detecting system for detecting the position of a reflection image of the cornea formed by the index projecting optical system, and including a detecting means and a measurement detecting circuit, a transmission control circuit, a first changing means for connecting the index projecting light source of the index projecting optical system to either the measurement control circuit or the transmission control circuit, a receiving detecting circuit, and a second changing means for connecting the detecting means of the detecting system to either the measurement detecting circuit or the receiving detecting circuit, the measurement unit transmitting a first optical signal containing measurement data when said index projecting light source is connected to the transmission control circuit, the printer unit comprising, a light receiving element for receiving the signal from the measurement unit, a receiving detecting circuit for detecting the optical signal received at the receiving element and transmitting the detected signal to a microcomputer, a communication control circuit connected to the microcomputer and outputting a communication signal in response to an output from the microcomputer; and a light emission element responsive to the communication signal from the communication control circuit for optically transmitting a second optical signal to the measurement unit.

According to the present invention, an ophthalmic apparatus of the hand-held type is easy to use and is provided with a system, including for instance a recorder and other circuits that are similar to conventional circuits, yet is further provided with a printing system for measurement data without spoiling advantages of hand-held apparatus, namely, small-size and light-weight.

BRIEF DESCRIPTION OF THE DRAWINGS

The accompanying drawings, which are incorporated in and constitute a part of this specification illustrate embodiments of the invention and, together with the description, serve to explain the objects, advantages and principles of the invention. In the drawings.

DETAILED DESCRIPTION OF THE PREFERRED EMBODIMENTS

A detailed description of preferred embodiments of an ophthalmic apparatus embodying the present invention will now be given referring to the accompanying drawings.

Figure 1:
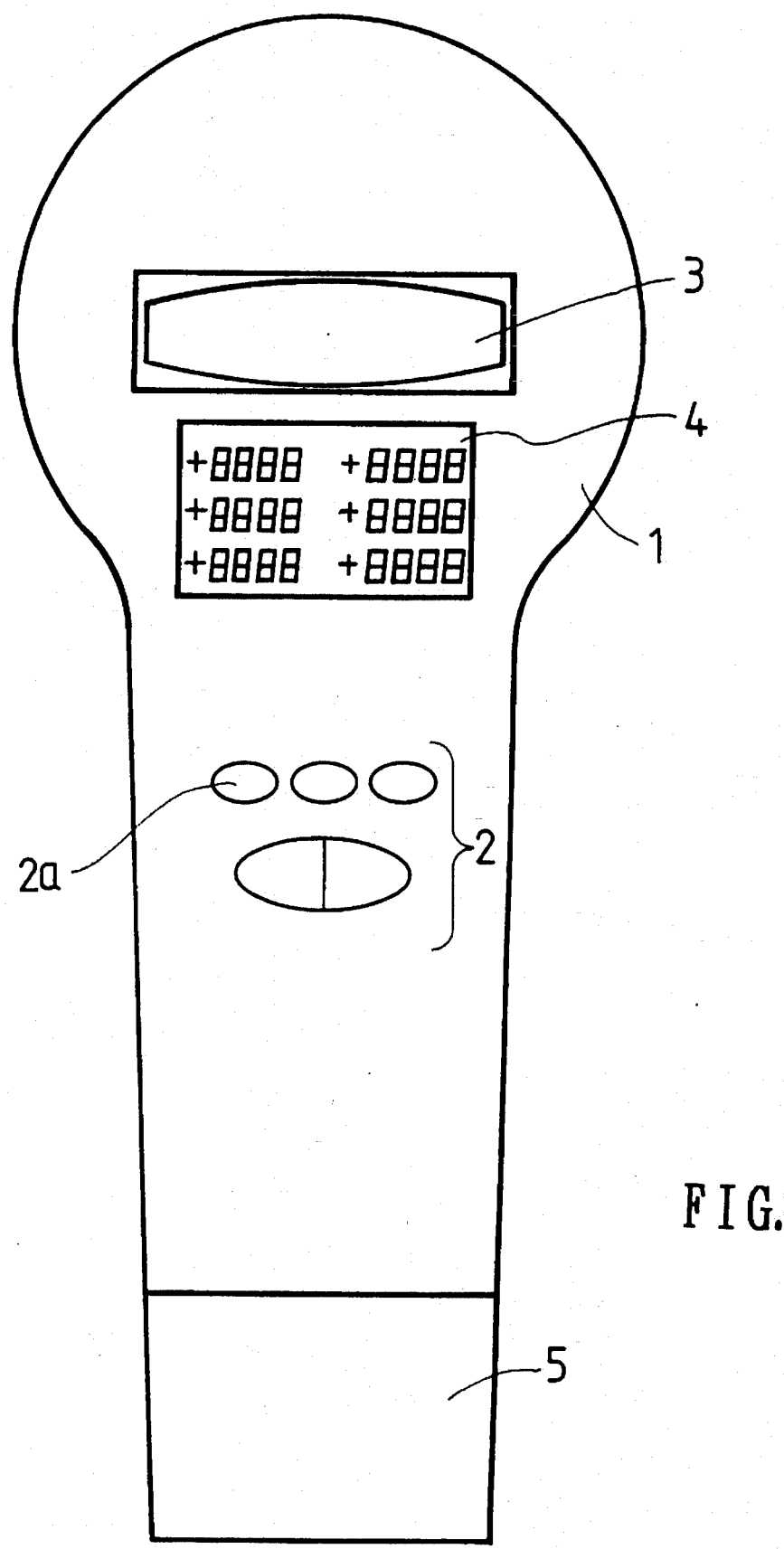
FIG. 1 is a schematic front view from the examiner's side of the first embodiment of a hand-held measurement unit made in accordance with the present invention.

FIG. 1 shows a measurement apparatus of the hand-held type in the first embodiment, taken from the examiner's side, for measuring the shape of the cornea. Measurement unit 1 provides internally an optical system for measurement and observation, and an electric system for control and calculation or the like. The measurement unit 1, on the examiner's side thereof, is provided with a group of operation buttons 2, in which a printing button 2a is for starting the communication to transmit measurement data to a printer unit as described below. Unit 1 also contains an observing window 3 through which an examinee's eye may be observed for proper alignment, and a liquid crystal display 4 for displaying measurement data. The lower part of the measurement unit 1 is shaped to form a hand-grip so that the measurement unit 1 may be held in one hand by the examiner, and a removable battery 5 is stored in the lower part of grip.

Figure 2:
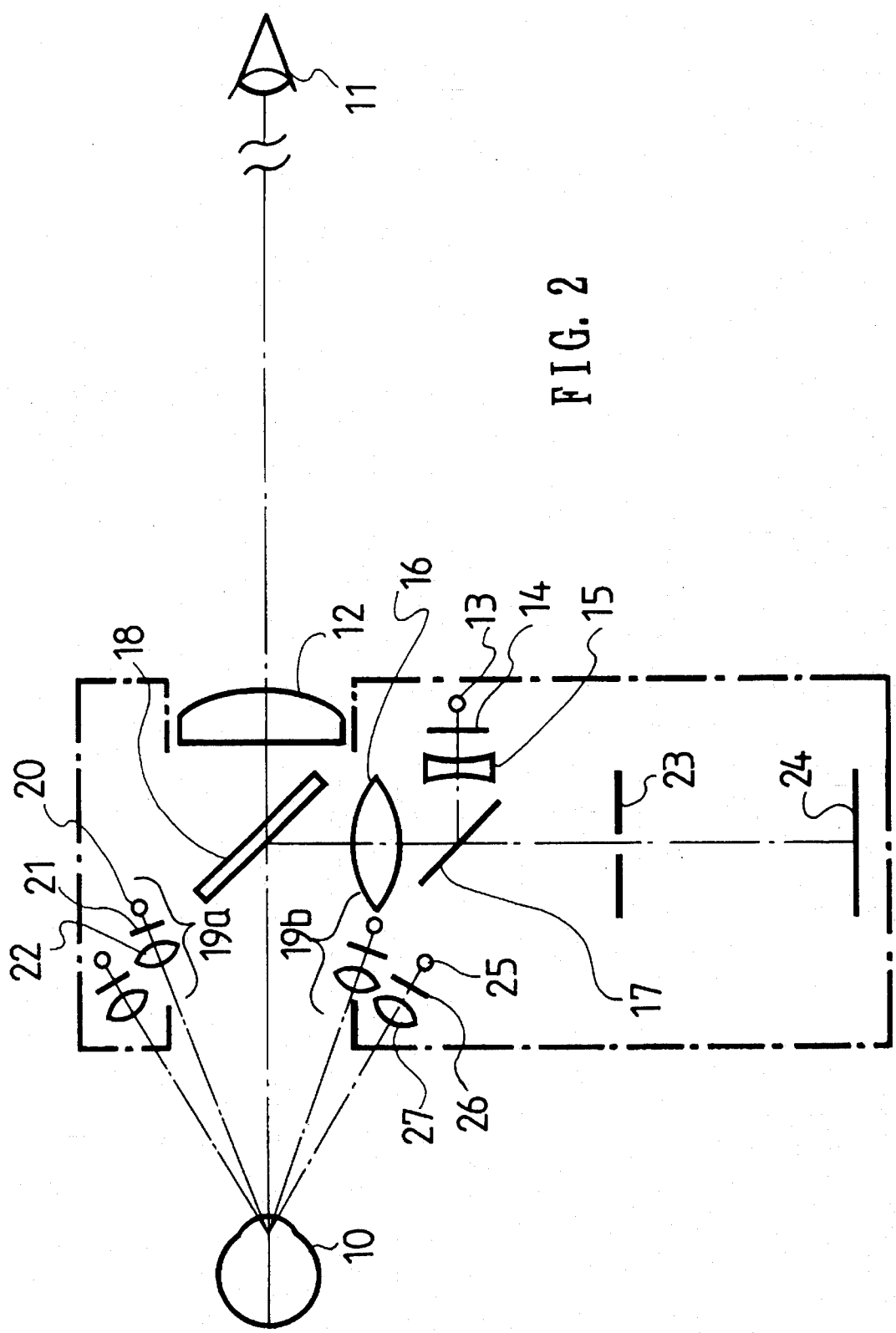
FIG. 2 is a schematic optical arrangement diagram of the hand-held ophthalmic apparatus in the first embodiment of the present invention.

FIG. 2 shows a schematic side view of an optical arrangement of an optical system contained within the hand-held measurement unit of FIG. 1. Numeral 10 is the examinee's eye to be measured and numeral 11 is the examiner's eye. The optical system comprises an observing lens 12 with which the examiner can magnify and observe the examinee's eye 10, a fixation index light source 13, a fixation index plate 14 having a spot aperture, a concave lens 15, an image forming lens 16, a dichroic mirror 17 and a beam splitter 18. Light from a light source 13 illuminates an index plate 14 and passes through an aperture of the index plate 14 and a concave lens 15, and then is reflected at a dichroic mirror 17 to an image forming lens 16. The light that passes through the image forming lens 16 is reflected by a beam splitter 18 toward the examinee's eye 10, and falls on the fundus of the eye 10 thereby to make the eye 10 fixedly look at the index plate 14.

Index projecting optical system 19 is for measuring corneal shape and is composed of four optical systems 19a–19d which are arranged at a 90-degree angle apart from each other in a circle, the center of which is an observing optical axis. Each of optical systems 19a–19d (19c and 19d are not shown in FIG. 2) is constituted of a LED 20 which emits light of near infrared wavelengths, a spot diaphragm 21 and a collimator lens 22. The LED 20 is utilized for the measurement light source and also for the data communication light source. Telecentric diaphragm 23 is disposed in the focal point of the image forming lens 16. Two-dimensional CCD imaging element 24 is for detecting positions of the corneal reflection images that are formed by the index projecting optical systems 19a–19d and also for receiving optical signal emitted from printer unit 30. The two-dimensional CCD imaging element 24 is conjugated with the iris or thereabout of the examinee's eye, on which cornea reflection images are to be formed through the image forming lens 16.

LEDs 25 are arranged apart at a 30-degree angle each in a circle around the observation optical axis, and each is provided with a spot diaphragm 26 and a collimator lens 27. The corneal reflection images formed by the LEDs 25 work in all as mire-ring.

Figure 3:
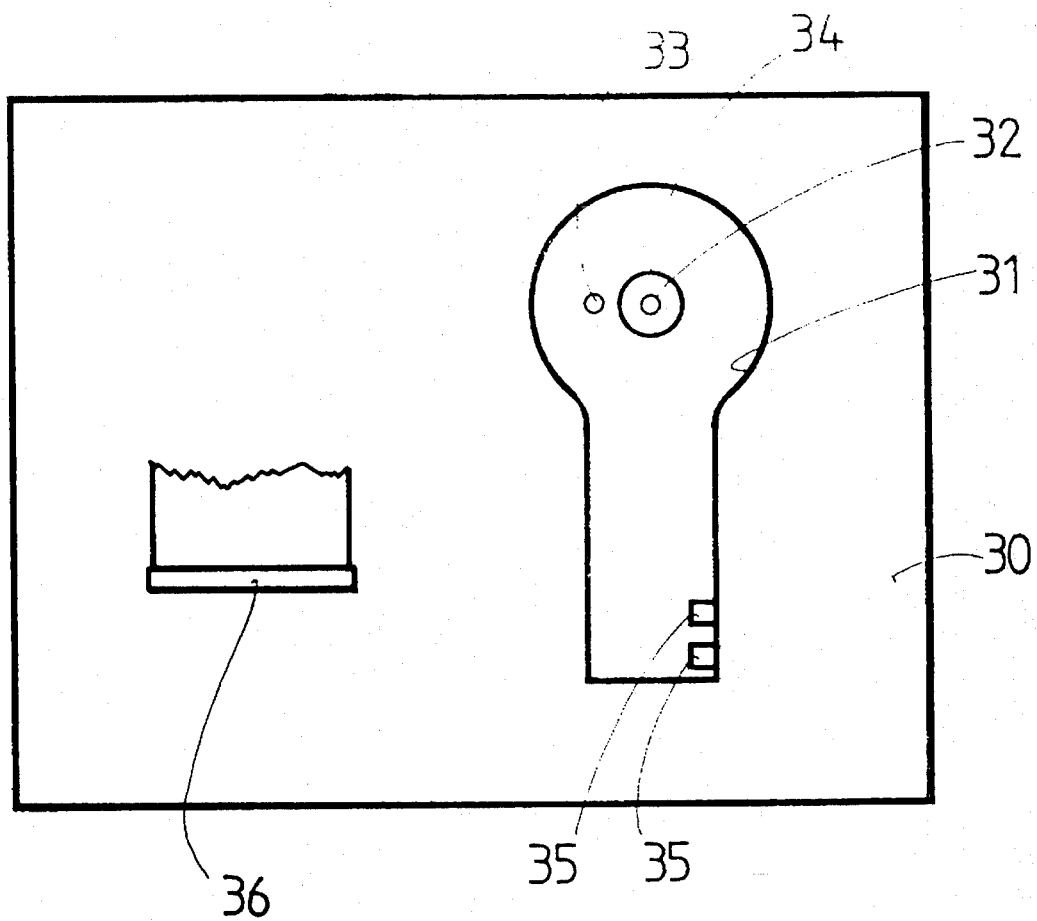
FIG. 3 is a schematic plan view of a printer unit made in accordance with the present invention.

In FIG. 3, shown is a printer unit 30 for printing out measurement data transmitted from the measurement unit 1 or transmitting measurement data to another computer. The printer unit 30 is provided with a measurement unit holder 31 on the upper plane, into which the measurement unit 1 can be inserted. Unit 1 is inserted face down on the side that faces to the examinee's eye. In the measurement unit holder 31, provided are a light emission element 32 for emitting infrared light along the optical axis the measurement optical system of the measurement unit 1, a light receiving element 33, a cylindrical barrier wall 34 for preventing crosstalk between light transmission from the measurement unit 1 to the printer unit 30 and the reverse transmission, and contacts 35 for charging the battery of unit 1.

The light receiving element 33 provided in the measurement unit holder 31 is disposed at a position facing to the LED 20d (not shown) of the index projecting optical system 19 (FIG. 2) when the measurement unit 1 is set into the printer unit 30. Charging of the battery 5 of the measurement unit 1 starts right after the measurement unit 1 is set into the printer unit 30.

The printer unit 30 includes also a printer 36 for printing out measurement data. The power supply for the printer unit 30 can be provided by cable through an AC adaptor, more usefully in moving, and preferably by battery as in the measurement unit 1 of this first embodiment, and also the printer unit 30 can be connected with a host computer by a communication cable (not shown).

Figure 4:
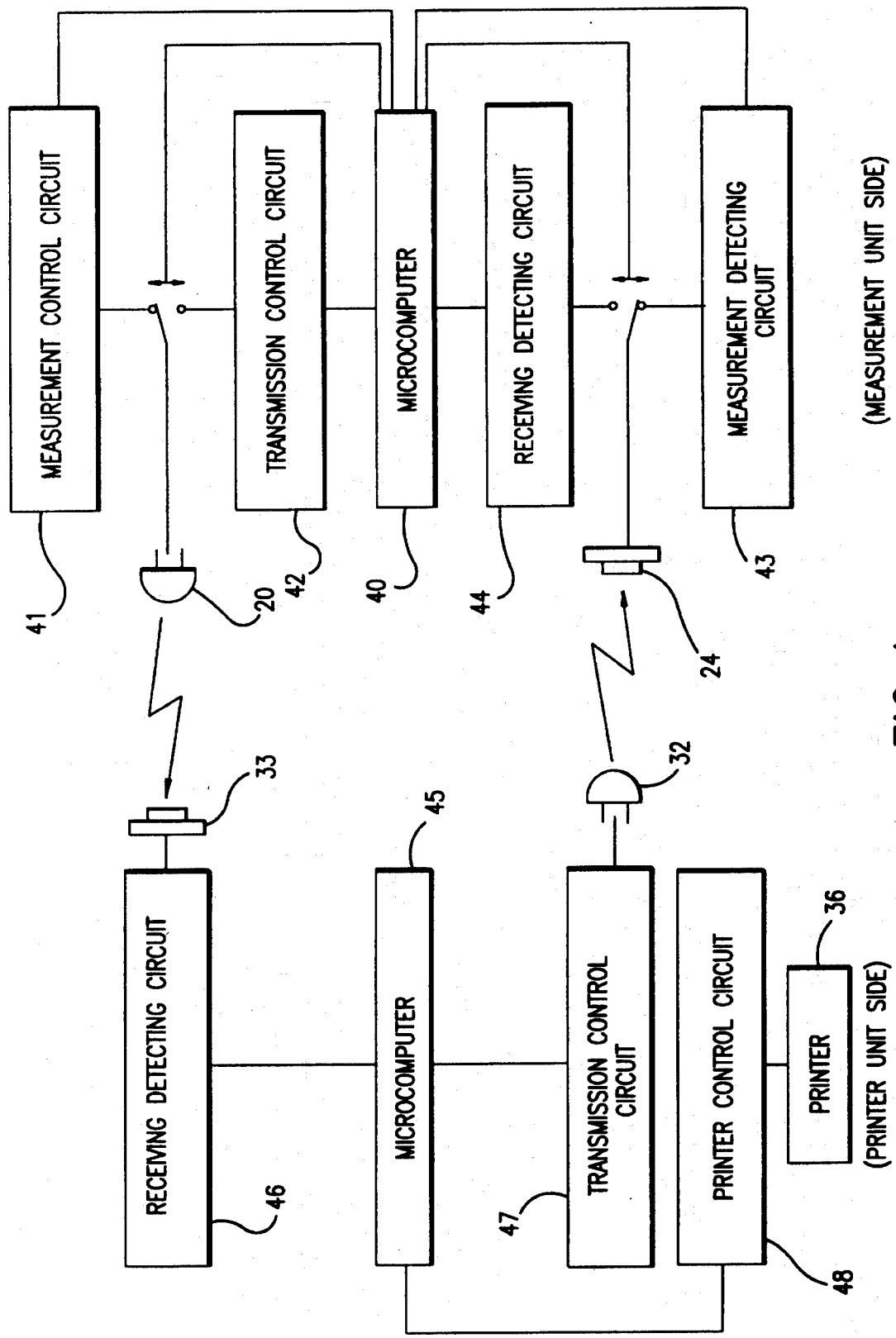
FIG. 4 is a block diagram for explaining the control system of the apparatus for optical communication of data in accordance with the present invention.

FIG. 4 shows a block diagram for explaining optical communication between the measurement unit 1 and the printer unit 30.

The measurement unit 1 is provided internally with a microcomputer 40 which changes the control circuit of the LED 20 from the measurement control circuit 41 to the transmission control circuit 42 and the reverse, on the basis of the mode signal (measurement or transmission mode signal). The microcomputer 40 connects the CCD imaging element 24 selectively with either the measurement detecting circuit 43 or the receiving detecting circuit 44.

The printer unit 30 is provided with a microcomputer 45. An optical communication signal emitted from the LED 20 is received at light receiving element 33 and transmitted through receiving detecting circuit 46 to the microcomputer 45. The microcomputer 45 modulates this communication signal into an optical communication signal through the transmission control circuit 47 and light emission element 32, and then transmits the optical communication signal to the measurement unit 1. Also, the printer 36 is driven by the microcomputer 45 through the printer control circuit 48.

The operation of the communication apparatus of FIG. 4, will be described below.

The shape of cornea of the examinee's eye is measured by the measurement unit 1, and the measurement data is stored in the microcomputer 40 of the measurement unit 1. If the print button 2a (FIG. 1) is not pressed then, the microcomputer 40 keeps the LED 20 connected with the measurement control circuit 41 and the CCD imaging element 24 connected with the measurement detecting circuit 43 respectively.

When the measurement unit 1 is set into the measurement unit holder 31 of the printer unit 30 (FIG. 3), the battery 5 of the measurement unit 1 makes contact with the contacts 35 of the printer unit 30, and thereby charging of the battery 5 starts.

If the print button 2a is now pressed after insertion of the measurement unit, the microcomputer 40 drives the LED 20 to connect with the transmission control circuit 42 and the CCD imaging element 24 to connect with the receiving detecting circuit 44 respectively, thus changing from a measurement mode to a print mode. The LED 20 emits a signal to the printer unit 30 to confirm whether the printer unit 30 has been prepared for receiving signal. The printer unit 30 receives the signal from the LED 20 at the receiving element 33 and emits a signal that preparation is complete through the light emission element 32 to the measurement unit 1. The CCD imaging element 24 receives the signal that the printer unit 30 is ready to receive data and the microcomputer 40 starts to transmit measurement data to the printer unit 30.

The microcomputer 45 of the printer unit 30 commands the transmission control circuit 47 to emit a signal of completion when the measurement data has been received through the receiving element 33 and the receiving detecting circuit 46 or a signal to retransmit when the measurement data has not been received. When the measurement unit 1 receives a signal of completion from the printer unit 30, power thereof is turned off. The microcomputer 45 of the printer unit 30 drives the printer 36 through the printer control circuit 48 to print out the measurement data.

Similarly, control information of the measurement unit 1 may be transmitted from the printer unit 30 to the measurement unit 1.

In the above embodiment, it is also possible to detect whether the measurement unit 1 is set in the holder 31 of the printer unit 30 and to change automatically into the communication mode if the measurement unit 1 is disposed at a predetermined position.

Communication between the measurement unit and the printer unit in the first embodiment is performed in a state where both units are in contact with each other, but both units may communicate with each other also in separate state, on condition that, preferably, the collimator lens 22 (FIG. 2) is removed and thereby communication rays are modulated into a divergent bundle of rays.

Figure 5:
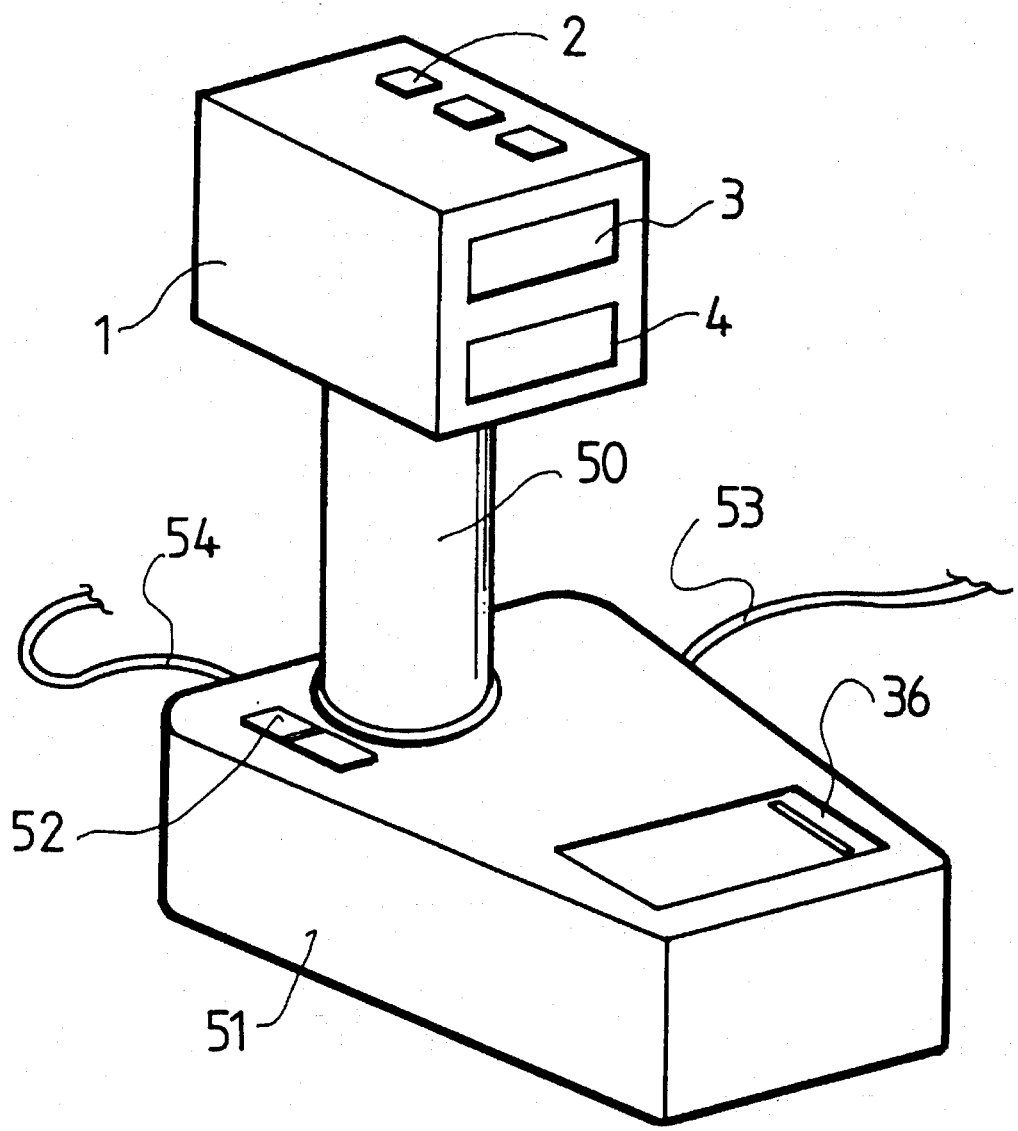
FIG. 5 is a perspective diagram of the second embodiment of a hand-held measurement unit and a receiving unit made in accordance with the present invention.

FIG. 5 shows a perspective view of the second embodiment of hand-held measurement apparatus for measuring the shape of the cornea and a receiving unit.

In FIG. 5, the measurement apparatus comprises a measurement unit 1 in the general shape of a box and a setting or receiving unit 51 in which the measurement unit 1 can be set. The measurement unit 1 is internally provided with an optical system for measuring and observing and electric systems for control, calculation and display, but the specific construction details of such systems is not explained in the present specification, being out of relation to an understanding of the present invention.

More specifically, the measurement unit 1 is provided with, on the enlarged, head part thereof, a group of operation switches 2, an observing window 3, and a liquid crystal display 4. A grip 50 is installed at the bottom of the measurement unit 1, so that the examiner can pull out the measurement unit 1 from the setting unit 51 by the grip 50 in one hand, and move about the measurement unit 1 freely.

In the setting unit 51, included are a printer 36 for recording measurement data and other data, a charge/power changing button 52, a power supplying cable 53 and a communicating cable 54 for connecting to the host computer. It is possible to change automatically between both the charging and power supplying modes by adding a charge changing circuit instead of the charge/power changing button 52.

Figure 6:
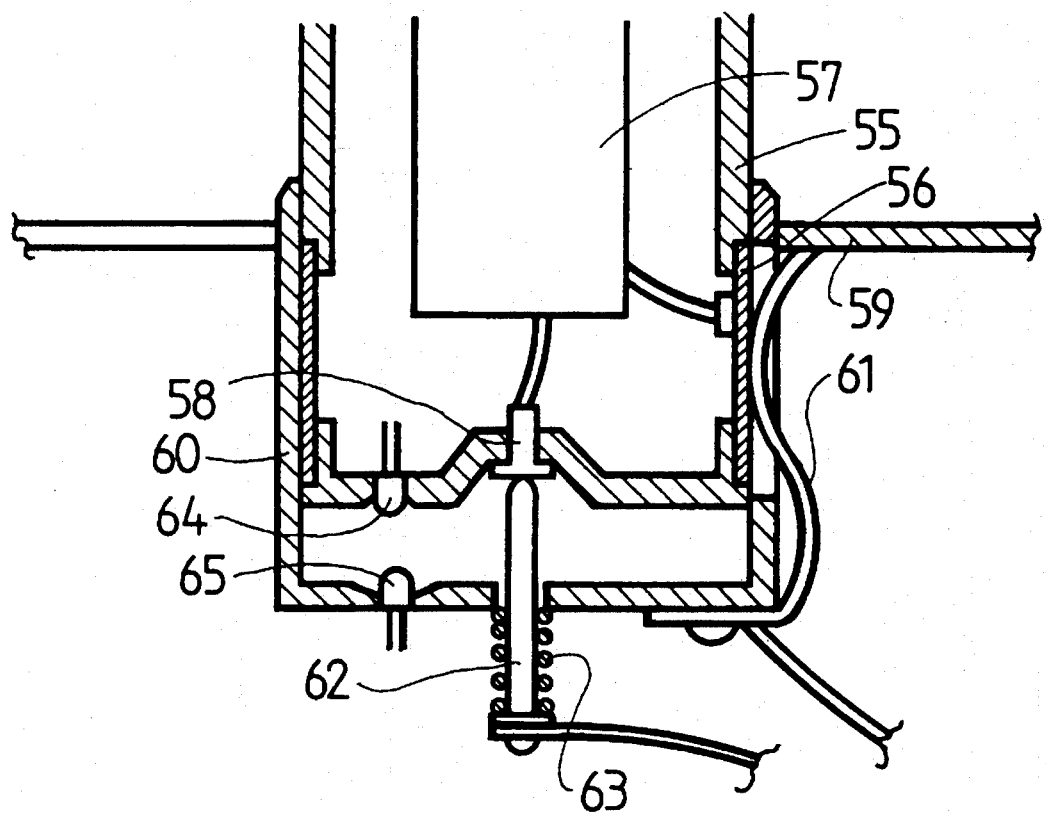
FIG. 6 is a partially sectional view of the embodiment of FIG. 5 showing the bottom of the hand-held unit sitting in the receiving unit.

FIG. 6 shows in partial section the construction of the measurement unit 1 in the setting unit 51 to permit both charging of the battery and data communication between the two units.

As shown in FIG. 6, the grip member 50 of the measurement unit is constituted of a cylindrical outer member 55 constructed partially as a conductor 56 at the lower part thereof, and inside retains a rechargeable battery 57 which is a Ni-Cd cell for example. The negative electrode of the rechargeable battery 57 is connected to the conductor 56 and the positive electrode is connected to positive terminal 58 which is fitted in the center of the bottom plane of the grip member 50.

The setting unit 51 is constituted of an upper plate 59 and supporting member 60 inwardly fixed in the upper plate 59. The supporting member 60 is to support and hold the cylindrical outer member 55 of the grip member 50. There is a slit in the cylindrical wall of the supporting member 60 so that the negative terminal 61 connected to the charging circuit is in contact with the conductor 56 of the grip member 50. Positive terminal 62 connected to the charging circuit extends upwardly through the bottom of the supporting member 60 so as to contact the positive terminal 58 set in the grip member 50. The positive terminal 62 is forced upward by a coil spring 63.

Incidentally, the grip member 50 of the second embodiment has a structure which may be set in the charging well provided in a conventional ophthalmic refraction stand, and the grip member 50 can be charged even by the charging well accordingly.

A light emission element 64 and a light receiving element 66 (not shown in FIG. 6, shown in FIG. 7) are provided in the bottom of the grip member 50, and correspondingly, a light receiving element 65 and a light emission element 67 (not shown in FIG. 6, shown in FIG. 7) are provided in the supporting member 60, each of which makes a pair with the receiving element 66 and the emission element 64, respectively. Mutual communication is performed in each pair of emission elements and receiving elements by transmitting and receiving signals therebetween.

Figure 7:
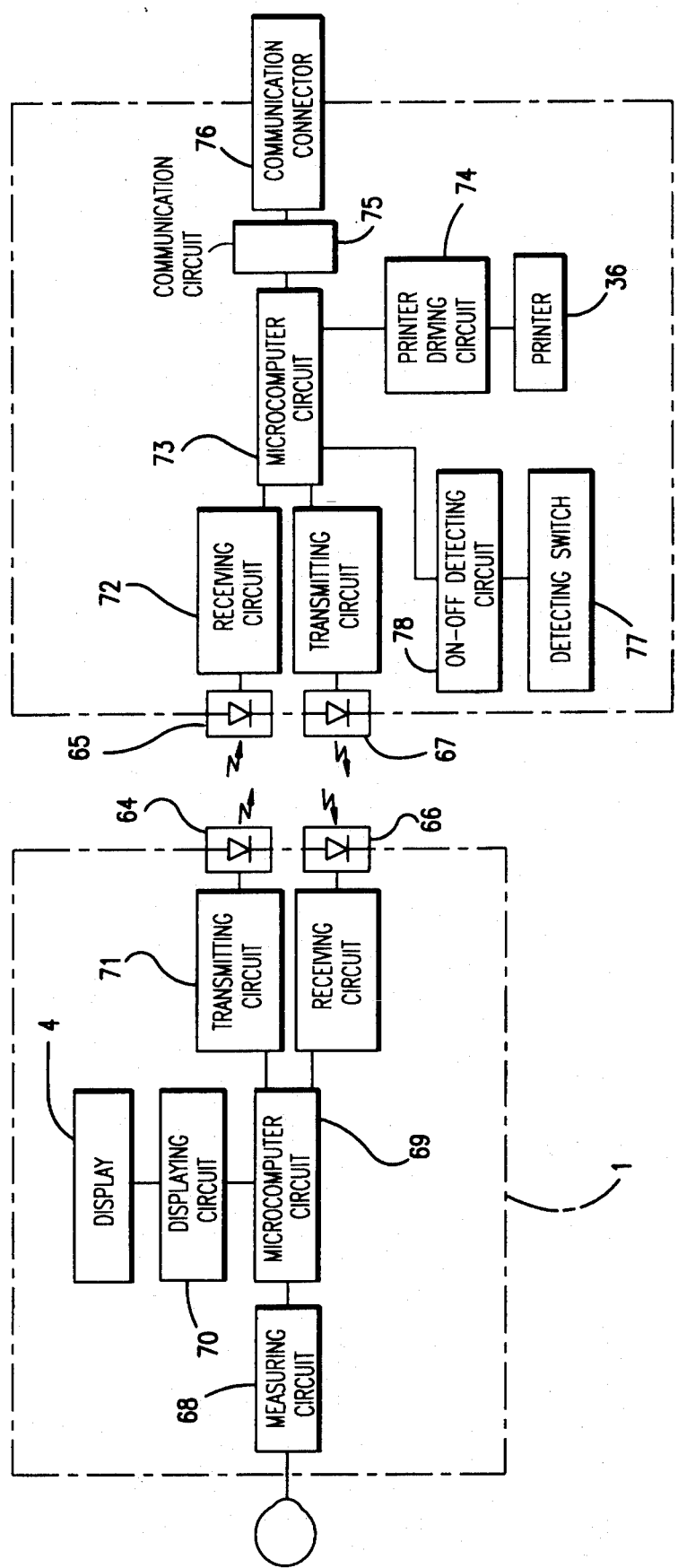
FIG. 7 is a block diagram for explaining the control system of the apparatus in the second embodiment for optical communication of data in accordance with the present invention.

The data communication circuit of the above-described apparatus in the second embodiment is explained with reference to FIG. 7 showing a block diagram.

The signal from the measurement system is processed at measurement circuit 68 and transmitted to microcomputer circuit 69. The microcomputer circuit 69 arithmetically processes the signal to obtain measurement data about radius of curvature of the cornea of the examinee's eye and the like, and then the measurement data is displayed in the liquid crystal display 4 through display circuit 70.

The measurement data processed in the microcomputer circuit 69 is further converted into optical communication signals through transmitting circuit 71 and the light emission element 64 and transmitted to the receiving element 65 of the setting unit 51. The optical communication signal received at the light receiving element 65 is processed in receiving circuit 72 and transmitted to microcomputer circuit 73. Then the microcomputer circuit 73 can transmit the measurement data to printer 36 through printer driving circuit 74, printing it out. Simultaneously, the measurement data processed in the microcomputer circuit 73 is transmitted through communication circuit 75 and communication connector 76 to a host computer (not shown).

The setting unit 51 further comprises detection switch 77 and on-off detecting circuit 78 thereof. The detection switch 77 is for detecting that the grip member 50 of the measurement unit 1 is set into the setting unit 51. Various switches except for the on-off switch may be utilized as a detection switch.

Operation of the above apparatus will be explained below.

After confirmation through charge condition detecting circuit (not shown) that the rechargeable battery 57 is so charged that the measurement unit is in usable state, first, the examiner pulls up the measurement unit 1 with the grip 50 in his hand, and then measures the examinee's eye with the measurement unit 1 using desired movements. The microcomputer circuit 69, then, arithmetically processes the return signals to obtain measurement data such as corneal radius of curvature and the like. The measurement data is displayed on the display 4. When a measurement is complete, the examiner inserts the grip member 50 into supporting member 60 of the setting unit 51 thereby to set the measurement unit 1 in the setting unit 51. Then, when grip 50 is detected in the setting unit 51, detecting switch 77 transmits a signal to request a start of transmission through the light emission element 67 to the receiving element 66. On receiving the signal from detecting switch 77, microcomputer circuit 69 transmits measurement data to setting unit 51.

In addition, hand-held type measurement apparatus will be, in the future, developed into various measurement apparatuses for eye refraction or the like and, if the structure of the grip member 50, communication code and print mode may be constituted in common among such hand-held type measurement units, for example by unifying communication code into ASCII code or providing convert system into common code, even one setting unit will be capable of charging, printing, and communicating with a host computer.

The present invention may be embodied in other specific forms without departing from the spirit or essential characteristics thereof. For instance, in the second embodiment mentioned above, communication of measurement data starts after confirming that the grip member 50 has been set into the setting unit 51, namely, the grip member 50 and the setting unit 51 are connected with each other, but also such communication can be performed where the grip member 50 receives signal from the setting unit 51 in a state where the grip member 50 is apart from the setting unit 51.

In the second embodiment, the command signal to start communication is transmitted from setting unit 51 and is intended to lighten the load imposed on rechargeable battery 57.

The foregoing description of the preferred embodiment of the invention has been presented for purposes of illustration and description. It is not intended to be exhaustive or to limit the invention to the precise form disclosed, and modifications and variations are possible in light of the above teachings or may be acquired from practice of the invention. The embodiment chosen and described are in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. An ophthalmic apparatus comprising:

(A) a hand-held measurement unit comprising (i) measurement means for projecting measurement light to an examinee's eye and detecting the measurement light reflected by the examinee's eye, and means for processing the detected measurement light to provide measurement data;

(ii) a hand-grip designed to be held by an examiner for placement of said measurement means;

(iii) wireless transmitting means for transmitting said measurement data to a receiving means separate from said measurement unit;

(iv) signal generating means for generating a start signal to initiate transmission of measurement data from the transmitting means;

(v) display means for displaying said measurement data; and (vi) a battery for supplying electric power to said measurement unit;

(B) a receiving device separate from said measurement unit and having said receiving means for receiving said measurement data; and a holding means for detachably holding the hand-held measurement unit during transmission of measurement data.

2. An ophthalmic apparatus according to claim 1, wherein said receiving device comprises a printing device for printing measurement data.

3. An ophthalmic apparatus according to claim 1, wherein said receiving device comprises wire communication means to input measurement data into a computer.

4. An ophthalmic apparatus according to claim 1, wherein the holding means includes a data receiving device for receiving data about the examinee's eye, and is provided with an optical transmitting means and an optical receiving means so that, when the measurement unit is held at a predetermined position in the holding means, wireless optical communication may be performed.

5. An ophthalmic apparatus according to claim 1, further comprising a light source for the measurement means, said light source used in common with the wireless transmitting means, and a mode changing switch and control circuit changing means for controlling the turning on and off of the light source by said mode changing switch thereby to permit switching between the measurement mode and wireless transmitting mode.

6. An ophthalmic apparatus according to claim 1, wherein the measurement unit includes optical receiving means and the receiving device includes optical transmitting means respectively.

7. An ophthalmic apparatus comprising:

(A) a hand-held measurement unit comprising:

(i) a measurement optical system for projecting luminous flux to an examinee's eye and receiving the luminous flux reflected by the examinee's eye at an optical detecting element, (ii) a hand-grip for supporting said measurement optical system, and designed to be held by an examiner in his hand, (iii) optical transmitting means for transmitting measurement data of the examinee's eye to an optical receiving means separate from said measurement unit, the measurement data being obtained based on reflected luminous flux received by the measurement optical system;

(iv) signal generating means for generating a start signal to initiate transmission of measurement data from the optical transmitting means;

(v) a light source for said measurement optical system, said light source used in common with the optical transmitting means; and (vi) a mode changing switch and control circuit changing means for controlling the turning on and off of the light source the mode changing switch thereby to permit switching between the measurement mode and the optical transmission mode, (B) a receiving unit having said optical receiving means for receiving said measurement data about the examinee's eye; and holding means for detachable holding the measurement unit during transmission of measurement data.

8. An ophthalmic apparatus comprising a measurement unit and a printer unit, said measurement unit being portable via one hand of an examiner and comprising:

an index projecting optical system for projecting index light for measuring the corneal shape of an examinee's eye, and including an index projecting light source and a measurement control circuit, a detecting system for detecting the position of a reflection image of the cornea formed by said index projecting optical system, and including a detecting means and a measurement detecting circuit, a transmission control circuit, a first changing means for connecting the index projecting light source of said index projecting optical system to either the measurement control circuit or the transmission control circuit, a receiving detecting circuit, and a second changing means for connecting the detecting means of said detecting system to either the measurement detecting circuit or the receiving detecting circuit, said measurement unit transmitting a first optical signal containing measurement data when said index projecting light source is connected to said transmission control circuit;

said printer unit comprising:

a light receiving element for receiving said optical signal from said measurement unit, a receiving detecting circuit for detecting the optical signal received at the receiving element and transmitting the detected signal to a microcomputer;

a communication control circuit connected to the microcomputer and outputting a communication signal in response to an output from the microcomputer; and a light emission element responsive to the communication signal from said communication control circuit for optically transmitting a second optical signal to the measurement unit.

9. An ophthalmic apparatus according to claim 8, wherein said printer unit is provided with a measurement unit holder for holding removably the measurement unit.

10. An ophthalmic apparatus according to claim 9, wherein said light emission element is disposed at a position where light is emitted along an optical axis of said detecting system when said measurement unit is being held in the holder in the printer unit.

11. An ophthalmic apparatus according to claim 9, wherein said light receiving element is disposed in a position opposite to the index projecting light source of said index projecting optical system when said measurement unit is being held in the holder in said printer unit.

12. An ophthalmic apparatus according to claim 9, wherein said measurement unit is internally removably provided with a battery to supply electric power to the measurement unit, and said measurement unit holder comprises a contact through which to charge said battery.

13. An ophthalmic apparatus according to claim 8, wherein said printer unit is provided with a printer for printing out measurement data which is received from said measurement unit.

14. An ophthalmic apparatus according to claim 8, wherein said measurement unit is provided with switch for switching one of measurement mode and between the communication mode.

* * * * *